United States Patent
Supronowicz

(10) Patent No.: US 10,906,852 B2
(45) Date of Patent: Feb. 2, 2021

(54) REMOVAL OF ALKYNE IMPURITIES FROM DIOLEFIN CONTAINING MIXTURES THROUGH CRACKING OVER CUO/AL2O3 BASED MATERIALS

(71) Applicant: SABIC Global Technologies B.V., Bergen op Zoom (NL)

(72) Inventor: Wojciech Supronowicz, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/500,573

(22) PCT Filed: Apr. 26, 2018

(86) PCT No.: PCT/IB2018/052914
§ 371 (c)(1),
(2) Date: Oct. 3, 2019

(87) PCT Pub. No.: WO2018/198072
PCT Pub. Date: Nov. 1, 2018

(65) Prior Publication Data
US 2020/0199047 A1    Jun. 25, 2020

Related U.S. Application Data

(60) Provisional application No. 62/490,794, filed on Apr. 27, 2017.

(51) Int. Cl.
*C07C 7/148* (2006.01)
*B01J 21/04* (2006.01)
(Continued)

(52) U.S. Cl.
CPC ............. *C07C 7/1485* (2013.01); *B01J 21/04* (2013.01); *B01J 23/72* (2013.01); *C10G 11/04* (2013.01);
(Continued)

(58) Field of Classification Search
CPC ... C07C 7/148; C07C 7/1485; C07C 2521/04; C07C 2523/72; B01J 21/04; B01J 23/72;
(Continued)

(56) References Cited

U.S. PATENT DOCUMENTS 2,398,301 A    4/1946  Frevel ........................... 585/800
2,953,608 A *  9/1960  Fernald .................. C07C 7/148
                                                           585/800
(Continued)

FOREIGN PATENT DOCUMENTS

CN          1230458 A       10/1999

OTHER PUBLICATIONS

Armbruster et al. "$Al_{13}Fe_4$ as a low-cost alternative for palladium in heterogeneous hydrogenation." Nature Materials, 11 (2012) 690-693.
(Continued)

*Primary Examiner* — In Suk C Bullock
*Assistant Examiner* — Jason Y Chong
(74) *Attorney, Agent, or Firm* — Norton Rose Fulbright US LLP

(57) ABSTRACT

Processes to selectively crack alkyne compounds from a hydrocarbon stream including olefinic and di-olefinic compounds are described. The process includes contacting the hydrocarbon stream with a supported CuO catalyst under conditions sufficient to crack the alkynes to form a product stream that included cracked compounds and further separating the cracked organic compounds from the hydrocarbon stream.

19 Claims, 1 Drawing Sheet

(51) Int. Cl.
*B01J 23/72* (2006.01)
*C10G 11/04* (2006.01)
*C10G 45/34* (2006.01)

(52) U.S. Cl.
CPC .......... *C10G 45/34* (2013.01); *C07C 2521/04* (2013.01); *C07C 2523/72* (2013.01); *C10G 2300/1092* (2013.01); *C10G 2300/4006* (2013.01); *C10G 2300/4012* (2013.01); *C10G 2300/4018* (2013.01); *C10G 2400/20* (2013.01)

(58) Field of Classification Search
CPC ............... C10G 11/04; C10G 45/34; C10G 2300/1092; C10G 2300/4006; C10G 2300/4012; C10G 2300/4018; C10G 2400/20
See application file for complete search history.

(56) References Cited

U.S. PATENT DOCUMENTS

| | | | |
|---|---|---|---|
| 3,105,858 A | 10/1963 | Kresge et al. | 585/259 |
| 3,492,366 A * | 1/1970 | Winter | C07C 7/148 208/295 |
| 3,754,050 A | 8/1973 | Duyverman | 260/681.5 |
| 4,174,355 A | 11/1979 | Patel et al. | 585/843 |
| 4,266,086 A | 5/1981 | Patel | 585/810 |
| 4,440,956 A | 4/1984 | Couvillion | 585/260 |
| 6,627,578 B2 | 9/2003 | Xu et al. | 502/331 |
| 7,393,993 B1 | 7/2008 | Kanazirev et al. | 585/809 |
| 8,680,350 B2 | 3/2014 | Hatscher et al. | 585/275 |

OTHER PUBLICATIONS

Comotti, M. "'Nano-design' as a Powerful Tool in Gold Catalyzed Oxidation Reactions." Ph.D. dissertation, Bochum, Germany 2007.
Duan et al. "A new microporous metal-organic framework with potential for highly selective separation methane from acetylene, ethylene and ethane at room temperature." Microporous and Mesoporous Materials, 190 (2014) 32-37.
Gao et al. "Preparation of heat-treated PAN/SiO$_2$ hybrid hollow fiber membrane contactor for acetylene absorption." Separation and Purification Technology, 159 (2016) 116-123.
International Search Report and Written Opinion from PCT/IB2018/052914 dated Jun. 15, 2018, 10 pages.
Jiang et al. "Adsorption separation of vinyl chloride and acetylene on activated carbon modified by metal ions." Journal of Industrial and Engineering Chemistry 20 (2014) 1693-1696.
Jung et al. "Highly efficient metal-free membranes for the separation of acetylene/olefin mixtures: Pyrrolidinium-based ionic liquids as acetylene transport carriers." Journal of Membrane Science, 354 (2010) 63-67.
Nikolaev et al. "Catalytic hydrogenation of alkyne and alkadiene impurities in alkenes. Practical and theoretical aspects." Russian Chemical Reviews, 78 (3) 231-247 (2009).
Palgunadi et al. "Ionic liquids for acetylene and ethylene separation: Material selection and solubility investigation." Chemical Engineering and Processing, 49 (2010) 192-198.
Piccolo, L. "Al$_{13}$Fe$_4$ selectively catalyzes the hydrogenation of butadiene at room temperature." Chemical Communications, 49 (2013) 9149-9151.
Torres Galvis, et al. "Supported Iron Nanoparticles as Catalysts for Sustainable Production of Lower Olefins." Science, 335 (2012) 835.
Wen et al. "High acetylene/ethylene separation in a microporous zinc(II) metal-organic framework with low binding energy." Chemical Communications, 52 (2016) 1166-1169.
Xia et al. "Microporous metal-organic frameworks with suitable pore spaces for acetylene storage and purification." Microporous and Mesoporous Materials, 215 (2015) 109-115.
Zhaksibaev et al. "Stereoselective hydrogenation of acetylene on copper catalysts: A quantum-chemical study." III International Conference "Catalysis: Fundamentals and Applications," Kinetics and Catalysis, Jul. 2008, vol. 49, Issue 4, pp. 527-530.

* cited by examiner

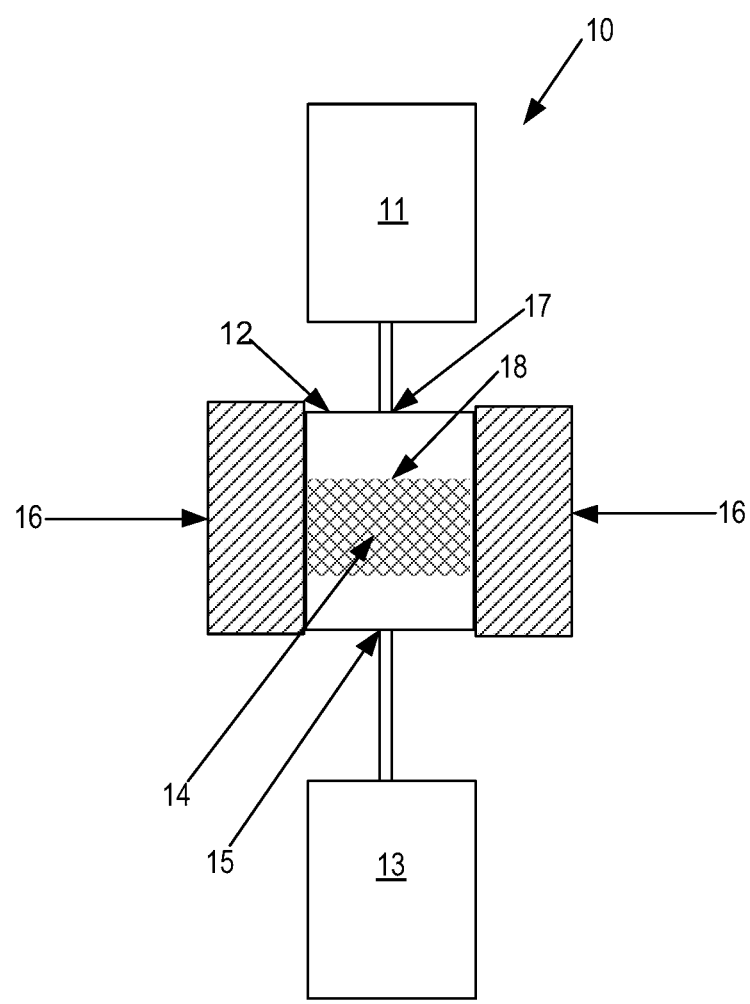

REMOVAL OF ALKYNE IMPURITIES FROM DIOLEFIN CONTAINING MIXTURES THROUGH CRACKING OVER CUO/AL2O3 BASED MATERIALS

CROSS REFERENCE TO RELATED APPLICATIONS

This application is a national phase application under 35 U.S.C. § 371 of International Application No. PCT/IB2018/052914 filed Apr. 26, 2018, which claims priority to U.S Provisional Patent Application No. 62/490,794 filed Apr. 27, 2017. The entire contents of each of the above-referenced disclosures is specifically incorporated by reference herein without disclaimer.

BACKGROUND OF THE INVENTION

A. Field of the Invention

The invention generally concerns the processes for removal of alkyne compounds from a hydrocarbon stream including olefinic and di-olefinic compounds. In particular, the invention concerns catalytically cracking a hydrocarbons stream that includes $C_4$ olefins and di-olefins, $C_5$ olefins and di-olefins, isoprene, and up to 3 wt. % alkynes with a supported CuO catalyst under conditions sufficient to crack the alkynes to organic compounds and separating the cracked organic compounds from the hydrocarbon stream.

B. Description of Related Art

Olefins and di-olefins are unsaturated compounds commonly used as feedstocks in many industrial applications. Conventionally, these unsaturated compounds are produced during cracking processes, which can also produce a range of impurities including alkynes. Although alkyne concentrations are less than 3 wt. % in cracked olefins, they can still present problems in downstream chemical processes (e.g., catalyst poison during polymerization, etc.), requiring further purification of the feedstocks containing them.

The known art is replete with processes to selectively remove alkynes from olefinic and di-olefinic mixtures. These processes can include extractive distillation, selective hydrogenation or oxidation, polymerization, and further cracking. Concerning cracking technologies, U.S. Pat. No. 4,266,086 to Patel et al. describes the removal of acetylenes from a stream comprising di-olefins at a temperature and pressures necessary to maintain the reaction (e.g., 93° C. to 127° C. (200 to 260° F.) and pressures of 0.7 MPa to 7 MPa (100 to 1000 psig)) using a copper oxide catalyst on a support with a contact time of 30 to 100 secs. Another disclosure by Patel et al. (U.S. Pat. No. 4,174,355) describes a process for removing α-acetylenes from di-olefins by contacting a hydrocarbon stream in the vapor phase with a supported-Group I B metal oxide catalyst (e.g., cupric oxide and silver oxide) in the absence of hydrogen, at a temperature in the range from 300 to 360° F. (i.e., 149 to 182° C.).

While several attempts to improve the practicality and effectiveness of alkyne removal from olefinic and di-olefinic feedstocks through cracking have been described, there is still a need to further increase catalytic activity of supported copper oxide materials in a cost effective and efficient manner and offer fine-tuned catalysts systems for specific feedstock compositions arising from a variety of commercial processes.

SUMMARY OF THE INVENTION

A solution to problems associated with removal of alkyne compounds from a hydrocarbon stream including olefinic and di-olefinic compounds discussed above has been discovered. The solution is premised on the use of supported copper oxide materials having increased catalytically activity and selectivity in cracking processes involving olefinic and di-olefinic feedstock that include $C_4$ olefins and di-olefins, $C_5$ olefins and di-olefins, isoprene, and up to 3 wt. % alkynes. In particular, supported CuO catalysts that include modified support, promoters or co-active phases, or combinations thereof, provide supported catalysts with increased activity and selectivity at lower reaction temperatures. Further the supported catalysts and process conditions can be fine-tuned to increase the efficiency of specific feedstock compositions arising from particular commercial processes (e.g., DCPD isoprene co-extraction process, etc.).

Embodiments of the present invention describe processes for removal of α and β alkyne compounds from a hydrocarbon stream that includes olefinic and di-olefinic compounds or olefinic, di-olefinic and aromatic compounds. A process can include contacting a hydrocarbon stream that includes $C_4$ olefins and di-olefins, $C_5$ olefins and di-olefins, paraffins, optional aromatics, and up to 3 wt. % alkynes with a supported CuO catalyst under conditions sufficient to crack the alkynes to form a product stream comprising cracked compounds; and separating the product stream from the hydrocarbon stream. The hydrocarbon stream can include 0.2 to 3 wt. % of the alkynes. The hydrocarbon stream can include 5 to 10 wt. % $C_4$ olefins and di-olefins (combined total), 30 to 50 wt. % $C_5$ olefins and di-olefins (combined total), 39 to 64 wt. % of aromatics and paraffins. In some embodiments, the hydrocarbon stream can include 6.5 to 7.8 wt. % $C_4$ olefins and di-olefins (combines total), 34 to 42 wt. % $C_5$ olefins and di-olefins (combined total), 39 to 43 wt. % $C_5$ paraffins, 10 to 14 wt. % isoprene, 0.2 to 0.9 wt. % alkynes, and 0.1 wt. % $C_{6+}$ compounds. Non-limiting examples of alkynes include 2-butyne, 1-butyne, propyne, pentyne or isomers thereof, or combinations thereof. In some embodiments, the hydrocarbons stream includes an inhibitor to inhibit polymerization of the di-olefins. The supported catalyst can include copper and a support, and an optional promoter. Promoters can include silver (Ag), platinum (Pt), palladium (Pd), manganese (Mn), cobalt (Co), nickel (Ni), chromium (Cr), molybdenum (Mo), or mixtures thereof. The catalyst support can include alumina, carbon, silica, zirconia, or combinations thereof. The cracking process can produce coke and hydrogen. The cracked compounds in the product stream can include alkanes and di-olefins. Alkanes can include methane, ethane, ethylene, or mixtures thereof. Di-olefins can include isoprene. In some embodiments, di-olefin loss from the hydrocarbon stream is less than 1 wt. % based on the total weight of the hydrocarbon stream. Cracking conditions can include a temperature of 120 to 225° C., preferably 160 to 185° C. and a pressure of 0.05 MPa to 0.5 MPa at a gas hourly space velocity of 280 to 400 $h^{-1}$ or a temperature of 100 to 125° C. and a pressure of 0.5 MPa to 2.5 MPa at a liquid hourly space velocity of 3 to 15 $h^{-1}$.

The following includes definitions of various terms and phrases used throughout this specification.

The term "catalyst" means a substance which alters the rate of a chemical reaction. "Catalytic" or "catalytically active" means having the properties of a catalyst.

The term "cracking" means to break a carbon-carbon bond of a hydrocarbon molecule to produce a hydrocarbon having fewer carbon atoms than the starting hydrocarbon molecule.

The terms "about" or "approximately" are defined as being close to as understood by one of ordinary skill in the art. In one non-limiting embodiment, the terms are defined to be within 10%, preferably within 5%, more preferably within 1%, and most preferably within 0.5%.

The terms "wt. %," "vol. %," or "mol. %" refers to a weight, volume, or molar percentage of a component, respectively, based on the total weight, the total volume of material, or total moles, that includes the component. In a non-limiting example, 10 grams of component in 100 grams of the material is 10 wt. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, includes any measurable decrease or complete inhibition to achieve a desired result.

The term "effective," as that term is used in the specification and/or claims, means adequate to accomplish a desired, expected, or intended result.

The use of the words "a" or "an" when used in conjunction with any of the terms "comprising," "including," "containing," or "having" in the claims, or the specification, may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The processes of the present invention can "comprise," "consist essentially of" or "consist of" particular ingredients, components, compositions, etc. disclosed throughout the specification. With respect to the transitional phase "consisting essentially of" in one non-limiting aspect, a basic and novel characteristic of the processes of the present invention are their ability to selective crack a hydrocarbon stream that includes $C_4$ olefins and di-olefins, $C_5$ olefins and di-olefins, paraffins, optional aromatics, and up to 3 wt. % alkynes.

In the context of the present invention at least eighteen embodiments are now described. Embodiment 1 is a process for removal of α and β alkyne compounds from a hydrocarbon stream containing olefinic and di-olefinic compounds or olefinic, di-olefinic and aromatic compounds. The process includes the steps of contacting a hydrocarbon stream containing $C_4$ olefins and di-olefins, $C_5$ olefins and di-olefins, aromatics, paraffins, and up to 3 wt. % alkynes with a supported CuO catalyst under conditions sufficient to crack the alkynes to form a product stream containing cracked compounds; and separating the product stream containing the cracked compounds from the hydrocarbon stream. Embodiment 2 is the process of embodiment 1, wherein the conditions sufficient to crack the alkynes to cracked compounds include a temperature of 100 to 125° C. and a pressure of 0.5 MPa to 2.5 MPa at a liquid hourly space velocity of 5 to 15 $h^{-1}$. Embodiment 3 is the process of any of embodiments 1 to 2, wherein the conditions sufficient to crack the alkynes to cracked compounds include a temperature of a temperature of 160 to 185° C. and a pressure of 0.05 MPa to 0.5 MPa at a gas hourly space velocity of 280 to 400 $h^{-1}$. Embodiment 4 is the process of any of embodiments 1 to 3, wherein the hydrocarbon feed contains 5 to 10 wt. % $C_4$ olefins and di-olefins, 30 to 50 wt. % $C_5$ olefins and di-olefins, 39 to 64 wt. % of aromatics and paraffins. Embodiment 5 is the process of any of embodiments 1 to 3, wherein the hydrocarbon feed wherein the hydrocarbon feed contains 6.5 to 7.8 wt. % $C_4$ olefins and di-olefins, 34 to 42 wt. % $C_5$ olefins and di-olefins, 39 to 43 wt. % $C_5$ paraffins, 10 to 14 wt. % isoprene, 0.2 to 0.9 wt. % alkynes, and 0.1 wt. % $C_{6+}$ compounds. Embodiment 6 is the process of any of embodiments 1 to 5, wherein the support of the supported CuO catalyst contains alumina, carbon, silica or zirconia or combinations thereof. Embodiment 7 is the process of any of embodiments 1 to 6, where the supported CuO catalyst is a $CuO/Al_2O_3$ catalyst Embodiment 8 is the process of any of embodiments 1 to 7, where the supported CuO catalyst further contains one or more promoters and/or co-active compounds. Embodiment 9 is the process of embodiment 8, wherein the promoters contain silver (Ag), platinum (Pt), palladium (Pd), manganese (Mn), cobalt (Co), nickel (Ni), chromium (Cr), molybdenum (Mo), or mixtures thereof. Embodiment 10 is the process of any of embodiments 1 to 9, further including an optional inhibitor to inhibit polymerization of the di-olefins. Embodiment 11 is the process of any of embodiments 1 to 10, wherein contacting further produces coke. Embodiment 12 is the process of any one of embodiments 1 to 11, wherein contacting further produces hydrogen gas. Embodiment 13 is the process of any one of embodiments 1 to 12, wherein the alkynes contain 2-butyne, 1-butyne, propyne, pentyne or isomers thereof, or combinations thereof. Embodiment 14 is the process of any one of embodiments 1 to 13, wherein the cracked compounds contain alkanes. Embodiment 15 is the process of embodiment 14, wherein the alkanes are methane, ethane, ethene, or mixtures thereof. Embodiment 16 is the process of any of embodiments 1 to 15, wherein the di-olefin loss from the hydrocarbon stream is less than 1 wt. % Embodiment 17 is the process of embodiment 16, wherein the di-olefin is isoprene. Embodiment 18 is the process of any one of embodiments 1 to 17, wherein the hydrocarbon stream contains 0.2 to 0.3 wt. % of the alkynes.

Other objects, features, and advantages of the present invention will become apparent from the following FIGURES, detailed description, and examples. It should be understood, however, that the FIGURES, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

Advantages of the present invention may become apparent to those skilled in the art with the benefit of the following detailed description and upon reference to the accompanying drawings.

FIG. 1 depicts a system for the removal of alkyne compounds from a hydrocarbon stream including olefinic and di-olefinic compounds.

While the invention is susceptible to various modifications and alternative forms, specific embodiments thereof are shown by way of example in the drawings. The drawings may not be to scale.

DETAILED DESCRIPTION OF THE INVENTION

Embodiments of the present invention include supported copper oxide based catalysts having increased activity and selectivity and in particular, their used to selectively crack alkynes from olefinic and di-olefinic feedstocks including $C_4$ olefins and di-olefins, $C_5$ olefins and di-olefins, paraffins, optional aromatics and up to 3 wt. % alkynes. The catalysts can be prepared by modern synthetic methods, by modification of support properties, by adding promoters or co-active phases, or combinations thereof. The processes according to the current invention make it possible to purify olefinic and di-olefinic feedstocks in an economical viable manner under low or high pressures.

These and other non-limiting aspects of the present invention are discussed in further detail in the following sections with reference to the FIGURES.

A. Alkyne Cracking Process

The reaction processing conditions in the continuous flow reactor or fixed bed reactor using the catalyst of the current invention can be varied to achieve a desired result. In a preferred aspect, alkyne compounds are removed from a hydrocarbon stream including olefinic and di-olefinic and di-olefinic and di-olefinic compounds under conditions sufficient to crack the alkynes to produce a product stream that includes cracked compounds with high selectivity and conversion. The process can include contacting a feed stream of olefinic and di-olefinic hydrocarbons with any of the catalysts described throughout the specification under conditions including temperature, contact time, hydrocarbon flow, concentration, and pressure. Cracking can be carried out at high pressures, (e.g., 0.5 to 2.5 MPa) or low pressures (e.g., 0.05 MPa to 0.5 MPa). In some embodiments, cracking conditions include a temperature of 100 to 125° C. and all values and ranges there between (e.g., 100, 105, 110, 115, 120, or 125° C.) at a pressure of 0.5 MPa to 2.5 MPa and all values and ranges there between (e.g., 0.5, 1, 1.5, 2, or 2.5 MPa). At these pressures and temperatures, the feed can be in the liquid phase and a liquid hourly space velocity can be 1 to 15 $h^{-1}$ and all values and ranges there between (e.g., 3, 4, 5, 6, 7, 8, 9, 10, 11, 12, 13, 14, or 15 $h^{-1}$). In some embodiments, cracking conditions include a temperature of 120-225° C., preferably 160 to 185° C. and all values and ranges there between (e.g., 120, 125, 130, 135, 140, 145, 150, 166, 160, 165, 170, 175, 180, or 185° C.) at a pressure of 0.05 MPa to 0.5 MPa and all values and ranges there between (e.g., 0.05, 0.1, 0.2, 0.3, 0.4, 0.5 MPa), preferably a temperature of 170 to 180° C., or about 176° C. At these pressures and temperatures, the hydrocarbon feed stream can be in the gas phase and a gas hourly space velocity can be 280 to 400 $h^{-1}$ and all values and ranges there between (e.g., 280, 290, 300, 310, 320, 330, 340, 350, 360, 370, 380, 390 or 400 $h^{-1}$). The alkynes in the hydrocarbon stream are converted, but other olefins and di-olefins are not converted. In some instances, a brief apparent contact time of the hydrocarbon stream with the supported catalyst may be required for removal of the alkyne impurities. The apparent contact time is defined as the length of time in seconds which a unit volume of gas, measured under the conditions of reaction, is in contact with the apparent unit volume of catalyst. The apparent contact time may be calculated, for instance, from the apparent volume of the catalyst bed, the average temperature and pressure of the reactor, and the flow rates in the reactor of the gaseous feed components. In a preferred instance, the cracking conditions can be performed under inert or non-oxidative conditions so inhibit formation of oxygenated organic compounds such as aldehydes and ketones. In a particular aspect, the di-olefin or isoprene loss from the hydrocarbon stream is less than 5 wt. %, 4 wt. %, 3 wt. %, 2 wt. %, and preferably less than 1 wt. %. The percent conversion of alkynes can be 70 to 90%, or about 80% at 176° C. and at a pressure of 0.05 MPa to 0.5 MPa.

The reaction of the methods and system of the present invention can occur in any type of reactor suitable for hydrocarbon cracking. The conditions mentioned above for purification of hydrocarbon streams may be varied based on the type of the reactor. In one aspect of the invention, the supported catalysts of the present invention can be used in continuous flow reactors to purify olefinic and di-olefinic mixtures. Non-limiting examples of the configuration of the supported catalysts in a continuous flow reactor are provided below and throughout this specification. The continuous flow reactor can be a fixed bed reactor, a stacked bed reactor, a fluidized bed reactor, or an ebullating bed reactor. In a preferred aspect of the invention, the reactor is a fixed bed reactor. The catalytic material can be arranged in the continuous flow reactor in layers (e.g., catalytic beds) or mixed with the reactant stream (e.g., ebullating bed). Any of the disclosed continuous flow reactor can further include a temperature controlled system fitted with regulators to maintain pressure during the reaction. The fixed bed reactor can include a chemically inert inner surface (e.g., a quartz inner lining). Without being limited by theory, some unsaturated hydrocarbons may adsorb onto the supported catalyst. The reaction conditions can be tuned so only alkynes adsorb onto the supported catalyst will undergo cracking and the olefinic and di-olefinic hydrocarbons will desorb unchanged. Additionally, alkanes present in the hydrocarbon feed can act as diluents and have no significant influence on the process. In some embodiments, used/deactived catalyst can be regenerated in a continuous process such as in a fluidized bed reactor. Products deposited on the supported catalyst can include, but not limited to, organic compounds, soot, and coke. The supported catalysts of the present invention can be regenerated several times without any measurable loss in activity. In some aspects, the catalyst bed can be placed over an adsorbent layer to further enhance removal of alkynes. For instance, a supported copper catalyst containing a mixture of alumina, silica, and magnesia may selectively adsorb alkynes from diene mixtures. The adsorbed alkynes can be removed with deposited products during the regeneration step.

The process can also include collecting or storing the product stream that includes the cracked products and or the hydrogen generated. Either of the product stream produced from the process of the current invention can be separated from each other or further purified using known gas/liquid or liquid/liquid separated techniques, for example, distillation, absorption, or membrane technology. For example, the product stream can exit the catalytic cracking reactor and enter a fractionation unit. In the fractionation unit, the hydrocarbons stream can be separated into a plurality of streams that can include, for example, a $C_4$ olefins and di-olefins stream and a $C_5$ olefins and di-olefins stream. The fractionation unit can be any fractionation unit known in the art capable of separating a hydrocarbons stream. Fractionation unit can include one or more units, one or more distillation plates, etc. At any point in time, the product stream can be recycled back into the cracking reactor. The product stream and/or reaction products can be analyzed during the reaction or after collection using known chromatography or spectroscopy methods. By way of example, in-line gas chromatography equipped with a thermal conductivity detector (TCD), a flame ionization detector (FID), and/or thermal conductivity detectors can be used to analyze the purity of the reaction products. In some embodiments, the catalytic cracking can be performed in the presence of water and/or a steam/water mixture.

Referring to FIG. 1, a system 10 is an illustration for removal of alkyne compounds from a hydrocarbon stream including olefinic and di-olefinic compounds using the supported catalysts of the present invention. The system 10 can include a hydrocarbon source 11, a reactor 12, and a collection device 13. The hydrocarbon source 11 can be configured to be in fluid communication with the reactor 12 via an inlet 17 on the reactor. The hydrocarbon source can be configured such that it regulates the amount of hydrocarbon feed entering the reactor 12. The reactor 12 can include a reaction zone 18 having the supported copper oxide catalyst 14 of the present invention (e.g., $CuO/Al_2O_3$ catalyst). The amounts of the hydrocarbon feed 11 and the catalyst 14 used can be modified as desired to achieve a given amount of product stream that includes cracked compounds by the system 10. The reactor 12 can include an outlet 15 for the product stream in the reaction zone 18. In embodiments when a fluidized bed catalytic cracker is used, the hydrocarbons stream can flow through the catalyst bed in an upwardly or downwardly direction. The products produced can include organic compounds derived from alkyne cracking. In some instances, a second collection device (not shown) can be used to collect the product stream. The collection device 13 can be in fluid communication with the reactor 12 via the outlet 15. Both the inlet 17 and the outlet 15 can be open and closed as desired. The collection device 13 can be configured to store, further process, or transfer desired purified hydrocarbons (e.g., olefins and di-olefins) for other uses. Still further, the system 10 can also include a heating source 16. The heating source 16 can be configured to heat the reaction zone 18 to a temperature sufficient (e.g., 100 to 250° C.) to crack the hydrocarbons. A non-limiting example of a heating source 16 can be a temperature controlled furnace. Additionally, any unreacted alkynes can be recycled and included in the hydrocarbon feed to further maximize the overall conversion. Further, certain olefins and/or diolefins can be separated by known processes in the art and used in other processes to produce commercially valuable chemicals. This increases the efficiency and commercial value of the cracking process of the present invention. In particular aspects, hydrocarbons source 11 can also be mixed with steam/water prior to entering reactor 12. In certain embodiments, steam/water can be added directly to reactor 12. Water/steam can be added in amounts of 20 wt. % to 30 wt. %, or about 25 wt. %.

B. Hydrocarbon Stream

The reactant mixture in the context of the present invention can be a gaseous or fluid mixture that includes, but is not limited to, hydrocarbon mixtures arising from cracking processes. In some aspects, the hydrocarbons stream can include a mixture of hydrocarbons having 1 to 10 carbon atoms ($C_1$ to $C_{10}$ hydrocarbons). Such a hydrocarbons stream can have a boiling point between 0° C. and 315° C. and can include straight chain acyclic alkanes (paraffins), cyclic alkanes (naphthenes), olefins, di-olefins, alkynes, aromatic hydrocarbons, and mixtures thereof. In some embodiments, the hydrocarbon stream can include $C_1$ to $C_{28}$ hydrocarbons, $C_2$ to $C_{15}$ hydrocarbons, $C_3$ to $C_{10}$ hydrocarbons, $C_4$ to $C_9$ hydrocarbons or any mixture thereof. In other embodiments, the hydrocarbons stream can include $C_4$ to $C_{6+}$ hydrocarbons and have a boiling point from 20° C. to 120° C. In a preferred aspect, the hydrocarbon stream to be purified can include alkanes (paraffins), alkenes (olefins), dienes (di-olefins), trienes (tri-olefins), tetraenes (tetra-olefins), etc., alkynes, diynes, triynes, etc., or compounds containing both alkenes and alkynes (e.g., vinylacetylene and the like). Simple $C_1$ to $C_5$ alkanes can include, for example, methane, ethane, propane, butane, isobutane, cyclopentane, etc. Simple $C_2$ to $C_5$ alkenes can include, for example, ethylene, propylene, cis-2-butene, 1-pentene, cyclopentene, 1-butene etc. Simple $C_2$ to $C_5$ alkynes and diynes can include, for example, acetylene, propyne, 1-butyne, 2-butyne, 1-pentyne, 2-pentyne, penta-1,3-diyne, etc. Specifically the hydrocarbon stream can includes $C_4$ olefins and di-olefins (e.g., 1-butene, cis-2-butene, trans-2-butene, 2-methylpropene, 1,2-butadiene, and 1,3-butadiene), $C_5$ olefins and di-olefins (e.g., pent-1-ene, 2-methylbut-2-ene, 2-methylbut-1-ene, (Z)-penta-2-ene, (E)-penta-2-ene, 3-methylbut-1-ene, penta-1,2-diene, (Z)-penta-1,3-diene, (E)-penta-1,3-diene, penta-1,4-diene, (Z)-penta-2,3-diene, (E)-penta-2,3-diene, 2-methylbuta-1,3-diene (isoprene), 3-methylbuta-1,2-diene, cyclopentene and cyclopentadiene etc.) and up to 3 wt. % alkynes. In the processing of $C_{5+}$ streams (e.g., hydrocarbons having at least 5 carbon atoms, "pyrolysis gasoline"), di- and polyenes such as pentadiene and cyclopentadiene, alkynes and/or aromatics with unsaturated substituents such as phenylacetylene and styrene, are undesired. In certain aspects, the hydrocarbon stream include 5 to 10 wt. % $C_4$ olefins and di-olefins, 30 to 50 wt. % $C_5$ olefins and di-olefins, 39 to 64 wt. % of aromatics and paraffins, preferably. In other aspects, the hydrocarbon stream can include 6.5 to 7.8 wt. % $C_4$ olefins and di-olefins, 34 to 42 wt. % $C_5$ olefins and di-olefins, 39 to 43 wt. % $C_5$ paraffins, 0.2 to 0.9 wt. % alkynes, and 0.1 wt. % $C_{6+}$ compounds. The amount of isoprene in the hydrocarbon stream can be 1 to 15 wt. %, or 1, 2, 3, 4, 5, 6, 7, 8, 9, 10, 11, 12, 13, 14, 15 wt. % or any range or value there between. In one embodiment, the hydrocarbon stream is produced from a dicyclopentadiene (DCPD) isoprene co-extraction process including 6.5 to 7.8 wt. % $C_4$ olefins and di-olefins, 34 to 42 wt. % $C_5$ olefins and di-olefins, 39 to 43 wt. % $C_5$ paraffins, 10 to 14 wt. % isoprene, 0.2 to 0.9 wt. % alkynes, and about 0.1 wt. % $C_{6+}$ compounds as represented in Table 1. In further aspects, the hydrocarbon feed stream may further include an optional inhibitor to inhibit polymerization of olefins and di-olefins. Possible inhibitors can include tricresyl phosphate (TCP) or sodium nitrate.

C. Supported Catalysts

1. Catalytic Material

The catalysts of the present invention include catalytic material and an underlying support. The catalytic material can include copper in the highest oxidation state, on a suitable catalyst support, that functions under conditions sufficient to crack alkynes in the presence of olefins to organic compounds, coke and hydrogen. The oxide used can include cupric oxide (CuO) on a catalyst support. Cupric oxide is most preferred for economic reasons. Unsupported cupric oxide catalyst is ineffective in this process, as is copper metal.

2. Support Material

The support material or a carrier can be porous and have a high surface area. A nonporous catalyst is effective for too short a period to be deemed economical in a commercial process. In some embodiments, the support is active (i.e., has catalytic activity). In other aspects, the support is inactive (i.e., non-catalytic). The support can be an inorganic oxide. In some embodiments, the support includes comprises an inorganic oxide, alpha, beta or theta alumina ($Al_2O_3$), activated $Al_2O_3$, silicon dioxide ($SiO_2$), titanium dioxide ($TiO_2$), magnesium oxide (MgO), calcium oxide (CaO), strontium oxide (SrO), zirconium oxide ($ZrO_2$), zinc oxide (ZnO), lithium aluminum oxide ($LiAlO_2$), magnesium aluminum oxide ($MgAlO_4$), manganese oxides (MnO, $MnO_2$, $Mn_2O_4$), lanthanum oxide ($La_2O_3$), activated carbon, silica gel, zeolites, activated clays, silicon carbide (SiC), diatomaceous earth, borates, magnesia, alumina-silica (aluminosilicates), calcium aluminate, or combinations thereof. In some aspects the support is or includes carbon, $Al_2O_3$, $ZrO_2$, $SiO_2$, or combinations thereof. Preferably the support is gamma alumina, preferably a CuO/gamma$Al_2O_3$ catalyst. The judicious selection of a support material or a combination of support materials can result in support catalysts with increased surface area and catalytic activity.

A wide range of particle sizes for the supported copper oxide catalyst may be used, depending in part upon process conditions dictated by the choice of a fixed bed reactor. In this process, a fluidized bed of catalyst is of no particular advantage over a fixed bed. Accordingly relatively large particles of catalyst are preferred, the particular size being chosen with due regard for pressure drop and heat transfer considerations.

Additional promoters or co-active phases can be used in combination with the catalysts of the present invention. The promoters or other additives can be mixed with the catalytic material or the supported catalysts of the present invention. The promoters or other additives can be active or inactive. In some instances, the addition of a promotor (e.g., $Ag_2O$) can influence the character of the catalytic material leading to improved catalytic activity. One or more of the additional promoters or other additives can include one or more alkali metals or alkali metal compounds thereof including lithium (Li), sodium (Na), potassium (K), rubidium (Rb), and cesium (Cs). One or more of the additional promoters or other additives can include one or more metals or metal compounds thereof including beryllium (Be), magnesium (Mg), calcium (Ca), strontium (Sr), barium (Ba), radium (Ra), scandium (Sc), yttrium (Y), lanthanides [i.e., lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu)], titanium (Ti), zirconium (Zr), Hafnium (Hf), vanadium (V), niobium (Nb), tantalum (Ta), chromium (Cr), molybdenum (Mo), tungsten (W), manganese (Mn), technetium (Tc), rhenium (Re), iron (Fe), ruthenium (Ru), osmium (Os), cobalt, (Co), rhodium (Rh), iridium (Ir), nickel (Ni), palladium (Pd), platinum (Pt), copper (Cu), silver (Ag), gold (Au), zinc (Zn), cadmium (Cd), mercury (Hg), aluminum (Al), gallium (Ga), indium (In), and thallium (Tl). Preferably, one or more of the additional promoters or other additives include Ag, Pt, Pb, Mn, Pd, Co, Ni, Cr, Bi, Zr or Mo. A non-limiting commercial source of the catalytic material, support material, and additional promoters/additives used in the current invention includes Sigma-Aldrich®, (U.S.A.), Alfa Aesar (U.S.A.), and Fischer Scientific (U.S.A.).

The amount of catalytic metal on the support material depends, inter alia, on the catalytic activity of the catalyst. In some embodiments, the amount of catalytic metal can range from about 0.1 wt. % to about 60 wt. %, with all ranges in between, for example from about 5 wt. % to about 50 wt. %, or about 2 wt. % to about 30 wt. %. In a preferred aspect, the amount of catalytic metal added to the catalyst ranges from about 1 wt. % to about 30 wt. % and is more specifically added to the catalyst at about 5 wt. %, about 10 wt. %, about 15 wt. %, about 20 wt. %, or about 15 wt. % based in each case on the total amount of the supported catalyst. To provide an economical process it is critical that the concentration of cupric oxide be in the range from 10 but less than 50 wt. % of supported catalyst. The supported catalyst may also generally include a support material in an amount that can range from about 20 wt. % to about 99 wt. %, with all ranges in between, for example from about 40 wt. % to about 95 wt. %, or about 50 wt. % to about 80 wt. %. In a preferred aspect, the amount of support material added to the catalyst ranges from about 70 wt. % to about 90 wt. % and is more specifically added to the catalyst at about 50 wt. %, about 75 wt. %, about 80 wt. %, about 85 wt. %, or about 95 wt. % based in each case on the total amount of the supported catalyst. The amount of promoters or other additives can range from about 0.001 wt. % to about 30 wt. %, with all ranges in between, for example from about 0.01 wt. % to about 20 wt. %, or about 0.1 wt. % to about 10 wt. %. In some embodiments, the amount of promoters or other additives added to the catalyst ranges from about 1 wt. % to about 5 wt. % and is more specifically added to the catalyst at about 1 wt. %, about 2 wt. %, about 3 wt. %, about 4 wt. %, or about 5 wt. % based in each case on the total amount of the supported catalyst.

D Preparation of Catalysts

All of the materials used to make the supported catalysts of the present invention can be purchased or made by processes known to those of ordinary skill in the art (e.g., precipitation/co-precipitation, impregnation, sol-gel, templates/surface derivatized metal oxides synthesis, solid-state synthesis, of mixed metal oxides, microemulsion technique, solvothermal, sonochemical, combustion synthesis, etc.). One manner of arriving at the oxides of the instant catalyst is by use of the water-soluble salts of copper and support materials, from which the oxides are precipitated in situ. Additional promoters or other additives can also be provided as salts and included in the precipitation. Prior to using the supported copper oxide catalysts of the present invention, the supported catalyst's activity can be enhanced by heating the catalyst at an elevated temperature. Supported catalysts can be oxidized/activated by heating or calcining in an appropriate atmosphere for a desired amount of time. Preferably, the catalyst is heated at a temperature in the range from about 200° C. to about 400° C. for from 1 to 24 hours, preferably 2 to 12 hours or 4 to 10 hours. If activity is insufficient, the catalyst can be heat-treated at even a higher temperature than 400° C. but well below a temperature deleterious to the catalyst, that is, a temperature at which the catalyst is deactivated, melted or decomposed.

The morphology, structure, and quality of the support copper oxide catalysts of the present invention can be evaluated using known material science methods and instrumentation. Non-limiting examples of such instrumentation include X-ray powder diffraction (XRD), gas adsorption analysis, scanning electron microscopy (SEM), high-resolution transmission electron microscopy (HRTEM), Raman spectroscopy, UV-VIS, optical reflectivity, optical microscopy, low-energy electron microscopy (LEEM), low-energy diffraction (LEED), atomic force microscopy (AFM), transmission electron microscopy (TEM), scanning tunnelling microscopy (STM), photoelectron microscopy (PES), angle-resolved photoelectron spectroscopy (ARPES), photoemission electron microscope (PEEM), energy dispersive X-ray spectroscopy (EDS, EDX, or XEDS), X-ray photoelectron spectroscopy (XPS), Image J data analysis software, reflection high-energy electron diffraction (RHEED), or microscope-based videography.

EXAMPLES

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

Example 1

Preparation of Catalysts

Commercially available spheroidal particles of Al$_2$O$_3$ were calcined at 636° C. for 6 hours, then optionally impregnated in solution of alkali or alkaline earth metal salt. The resulting support can then be dried and calcined at 200 to 400° C. for 2 to 12 hours and then, impregnated in a formulated solution of copper nitrate so the copper content is 14 wt. %, based on the total weight of the supported catalyst. The resulting support was calcined at 300 to 600° C. for 2 to 12 hours.

Example 2

Alkyne Cracking Low Pressure Process

Evaluation can be carried out in a high throughput fixed bed reactor setup housed in a temperature controlled system fitted with regulators to maintain pressure during the reaction for. The output streams can be analyzed by online GC analysis. A CuO (14 wt. %) on gamma Al$_2$O$_3$ support (1.98 g, with an average particle size of 410-220 microns) was positioned in the middle of a clean and dry tubular reactor, with a thermocouple positioned inside the catalyst bed. A synthetic hydrocarbon feed was prepared by mixing 72.57 wt. % wt. % hexane, 12.5 wtwt. % isoprene, 14.5 wtwt. % isopentane, 0.43 wtwt. % 2-butyne together at 6° C. The hydrocarbon feed was held in a container at 6° C. to minimize volatization of the hydrocarbons. The catalyst in the reactor was preconditioned by heating the reactor to 200° C. and holding for 2 h. The heating lines before the reactor were set at 165° C. and the heating lines after the reactor were set at 140° C. The hydrocarbon feed was fed to the reactor at a set weight hourly space velocity (WHSV). The product stream exiting the reactor was collected in a container and held at 10° C. The reaction was run for 4 hours. Table 1 lists the results for the runs at 165° C. and WHSV of 12, and 176° C. and WHSV of 4.4. From the data in Table 1, 90 wtwt. % of the alkynes were cracked with an isoprene loss of less than 1 wtwt. % at 176° C. and WHSV of 4.4.

TABLE 1

| 2-Butyne Conversion (%) | Isoprene loss (wt. %) |
|---|---|
| T = 165° C.; WHSV = 12 | |
| <3 | 0 |
| T = 176° C.; WHSV = 4.4 | |
| 90 | 0.4 |

TABLE 1-continued

| 2-Butyne Conversion (%) | Isoprene loss (wt. %) |
|---|---|
| No Catalyst | |
| 8 | 0 |
| Al$_2$O$_3$ | |
| 10 | 0 |

Example 3

Alkyne Cracking Elevated Pressure Process

Evaluation was carried out in a high throughput fixed bed reactor setup housed in a temperature controlled system fitted with regulators to maintain pressure during the reaction for. The output streams was analyzed by online GC analysis. A CuO (14 wt. %) on gamma Al$_2$O$_3$ support (2.37 g, with an average particle size of 410-220 microns) was positioned in the middle of a clean and dry tubular reactor, with a thermocouple positioned inside the catalyst bed. A synthetic hydrocarbon feed was prepared by mixing 72.5 wt. % hexane, 12.5 wt % isoprene, 14.5 wt % isopentane, 0.5 wt % 2-butyne together at 6° C. The hydrocarbon feed was held in a container at 6° C. to minimize volatization of the hydrocarbons. The catalyst in the reactor was preconditioned by heating the reactor to 200° C. and holding for 2 h. The heating lines before the reactor were set at 120° C. and the heating lines after the reactor were set at 120° C. The hydrocarbon feed was fed to the reactor at a set liquid hourly space velocity (LHSV). The reaction was conducted under elevated pressure of 10.34 Bar (150 PSI). The product stream exiting the reactor was collected in a container and held at 10° C. The reaction was run for 3 hours. Table 2 lists the results for the runs at 120° C. and LHSV of 5 and 8, and 110° C. and LHSV of 4. From the data in Table 2, 91 wt. % of the alkynes were cracked with an isoprene loss of less than 1 wt. % at 110° C., LHSV of 4 and pressure of 10.34 Bar (150 PSI).

TABLE 2

| 2-Butyne Conversion (%) | Isoprene loss (wt. %) |
|---|---|
| T = 120° C.; LHSV = 5; P = 150 PSI | |
| 53 | 10 |
| T = 120° C.; LHSV = 8; P = 150 PSI | |
| 0 | 0 |
| T = 110° C.; LHSV = 4; P = 150 PSI | |
| 91 | 0.9 |

The invention claimed is:
1. A process for removal of alkyne compounds from a hydrocarbon stream, the process comprising:
contacting a hydrocarbon stream comprising 5 to 10 wt. % C$_4$ mono-olefins and di-olefins, 30 to 50 wt. % C$_5$ mono-olefins and di-olefins, 39 to 64 wt. % aromatics and paraffins, and up to 3 wt. % alkynes with a supported CuO catalyst under conditions sufficient to crack the alkynes to form a product stream comprising cracked compounds; and
recovering the product stream comprising the cracked compounds.

2. The process of claim 1, wherein the conditions sufficient to crack the alkynes to form the product stream comprising the cracked compounds comprise a temperature of 100 to 125° C. and a pressure of 0.5 MPa to 2.5 MPa at a liquid hourly space velocity of 5 to 15 $h^{-1}$.

3. The process of claim 2, wherein the hydrocarbon stream comprises 0.2 to 0.3 wt. % of the alkynes.

4. The process of claim 1, wherein the conditions sufficient to crack the alkynes to form the product stream comprising the cracked compounds comprise a temperature of a temperature of 160 to 185° C. and a pressure of 0.05 MPa to 0.5 MPa at a gas hourly space velocity of 280 to 400 $h^{-1}$.

5. The process of claim 4, wherein the hydrocarbon stream comprises 0.2 to 0.3 wt. % of the alkynes.

6. The process of claim 1, wherein the hydrocarbon feed comprises 6.5 to 7.8 wt. % $C_4$ mono-olefins and di-olefins, 34 to 42 wt. % $C_5$ mono-olefins and di-olefins, 39 to 43 wt. % $C_5$ paraffins, 10 to 14 wt. % isoprene, 0.2 to 0.9 wt. % alkynes, and 0.1 wt. % $C_{6+}$ compounds.

7. The process of claim 1, wherein a support of the supported CuO catalyst comprises alumina, carbon, silica or zirconia or combinations thereof.

8. The process of claim 1, where the supported CuO catalyst is a $CuO/Al_2O_3$ catalyst.

9. The process of claim 1, where the supported CuO catalyst further comprises one or more promoters and/or co-active compounds.

10. The process of claim 9, wherein the promoters comprise silver (Ag), platinum (Pt), palladium (Pd), manganese (Mn), cobalt (Co), nickel (Ni), chromium (Cr), molybdenum (Mo), or mixtures thereof.

11. The process of claim 1, wherein the hydrocarbon stream further comprises an optional inhibitor to inhibit polymerization of the $C_4$ and/or $C_5$ di-olefins.

12. The process of claim 1, wherein the contacting further produces coke.

13. The process of claim 1, wherein the contacting further produces hydrogen gas.

14. The process of claim 1, wherein the alkynes comprise 2-butyne, 1-butyne, propyne, pentyne or isomers thereof, or combinations thereof.

15. The process of claim 1, wherein the cracked compounds comprise alkanes.

16. The process of claim 15, wherein the alkanes are methane, ethane, ethene, or mixtures thereof.

17. The process of claim 1, wherein a di-olefin loss from the hydrocarbon stream is less than 1 wt. %.

18. The process of claim 17, wherein the di-olefin loss is an isoprene loss.

19. The process of claim 1, wherein the hydrocarbon stream comprises 0.2 to 0.3 wt. % of the alkynes.

* * * * *